United States Patent [19]

Fujishima et al.

[11] Patent Number: 5,252,468

[45] Date of Patent: Oct. 12, 1993

[54] **PROCESS FOR PRODUCING DEACETYLASE FROM *VIBRIO CHOLEREA* IFO 15429**

[75] Inventors: Shizu Fujishima, Ikeda; Fumiko Yaku, Suita; Ryutarou Tanaka, Osaka; Einosuke Muraki, Osaka; Naoko Yamano, Osaka, all of Japan

[73] Assignee: Agency of Industrial Science & Technology, Tokyo, Japan

[21] Appl. No.: 842,304

[22] Filed: Feb. 26, 1992

[30] Foreign Application Priority Data

May 27, 1991 [JP] Japan .................. 3-152595

[51] Int. Cl.$^5$ .......... C12N 9/06; C12N 9/00; C12P 19/26; C12P 21/04
[52] U.S. Cl. .................. 435/71.1; 435/191; 435/84; 435/183
[58] Field of Search ........... 435/183, 191, 71.1, 435/84

[56] References Cited

U.S. PATENT DOCUMENTS 4,958,011 9/1990 Bade ........................ 536/20
5,061,627 10/1991 Olsen et al. ............... 435/183

FOREIGN PATENT DOCUMENTS 8500109 1/1985 World Int. Prop. O. ........ 536/20

*Primary Examiner*—Douglas W. Robinson
*Assistant Examiner*—Deborah K. Ware
*Attorney, Agent, or Firm*—Armstrong, Westerman, Hattori, McLeland & Naughton

[57] ABSTRACT

A process for producing deacetylase which comprises incubating a deacetylase-producing bacterium belonging to Vibrio cholerae in a IFO 15429 culture medium containing a carbon source, a nitrogen source, an inorganic salt and an inducer for producing the deacetylase and isolating the deacetylase from cells separated from said culture medium.

1 Claim, No Drawings

PROCESS FOR PRODUCING DEACETYLASE FROM VIBRIO CHOLEREA IFO 15429

BACKGROUND OF THE INVENTION

This invention relates to a process for producing deacetylase by incubating a deacetylase-producing bacterium belonging to Vibrio sp.

The term "deacetylase" as used herein means an enzyme capable of deacetylating N-acetylglucosamine, oligomers thereof or chitin.

In recent years, chitin, which is a biomass resource following cellulose, and chitosan, which is a deacetylation product thereof, have attracted public attention as polysaccharides having a number of useful functions. It has been found out, in particular, that chitosan of a low molecular weight (i.e., a glucosamine oligomer) has potent antimicrobial and antitumor activities per se and, furthermore, serves as an elicitor capable of inducing the production of a substance having an antimicrobial activity.

Compared with chitin, chitosan homologs are highly soluble and thus have become more and more important as a starting material for producing a number of useful substances.

Chitosan has been produced by removing inorganic salts, proteins and lipids from the cuticle (crust) of a crustacean such as prawn or crab and heating the purified chitin thus obtained in a concentrated alkali solution of 30 to 60%. Namely, chitosan is deacetylated chitin.

When heated in the aforesaid concentrated alkali solution, however, the chitin undergoes decomposition of the main chitin chain simultaneously with the deacetylation, which causes such a problem that the yield of the target chitosan is lowered while the amounts of by-products are increased.

There has been known a biological method for deacetylating chitin with the use of deacetylase or a microorganism capable of producing this enzyme.

There has been reported no example of this biological method, except one wherein a microorganism of Mucor sp. is used, one wherein a microorganism of Aeromonas sp. is used and one wherein a microorganism of Colletotrichum sp. is used.

With the use of the microorganism of Mucor sp., soluble glycol chitin and the pentamer can be deacetylated to the extent of 12 to 14%. However other oligosaccharides and solid chitin can be deacetylated thereby to the extent of as low as 0 to 5% [refer to Y. Araki, E. Ito, Eur. J. Biochem., 55, 71 (1975)].

The microorganism of Aeromonas sp. is a strain searched for in order to treat exclusively solid chitin of a high degree of polymerization. Therefore nothing is reported relating to the effects of this microorganism on oligosaccharides [refer to K. Shimabara, K. Iwasaki, Reports of the Asahi Glass Foundation for Industrial Technology, 41, 299 (1982)].

The microorganism of Colletotrichum sp., which suffers from a decrease in the activity at 30° C., should be incubated at a relatively low temperature (e.g., 25° C.). Thus the deacetylation with the use of this microorganism requires a long period of time (about 5 days). In addition, it has only a low deacetylation activity on N-acetylglucosamine trimer or dimer. Namely, the ratios of its deacetylation activity on the trimer and the dimer, based on that on the pentamer, are respectively 6% and 1% [refer to H. Kauss, B. Bauch, Methods in Enzymology, 161, 518 (1988)].

SUMMARY OF THE INVENTION

It is an object of the present invention to provide a process for producing deacetylase whereby chitosan, glucosamine and glucosamine oligomers can be easily produced from chitin, N-acetylglucosamine and N-acetylglucosamine oligomers under mild conditions without being accompanied by any side reactions.

The aforesaid object of the present invention can be achieved by incubating a deacetylase-producing bacterium belonging to Vibrio sp. in a medium containing a carbon source, a nitrogen source, an inorganic salt and an inducer for producing the deacetylase, dividing said medium into a solution and cells and then isolating the deacetylase from and said cells.

PREFERRED EMBODIMENTS OF THE INVENTION

The present invention has been completed based on a finding that a strain belonging to Vibrio sp. can produce deacetylase. As an example of this deacetylase-producing bacterium, Vibrio cholerae non-O1, which has been known per se, may be cited.

Next, the conditions for incubating the deacetylase-producing bacterium, a method for isolating the deacetylase, and the properties of the deacetylase, will be described in detail by taking a case, wherein Vibrio cholerae non-O1 is employed, as an example. (1) Incubation conditions.

A medium for incubating Vibrio cholerae non-O1 may be prepared by adding an inducer to a medium containing a carbon source, a nitrogen source and an inorganic salt. As the inducer, at least one substance selected from the group consisting of chitin, chitin-containing materials, N-acetylglucosamine and N-acetylglucosamine oligomers may be used. Examples of the chitin-containing materials include the cuticle of, for example, crab, prawn or cuttlefish and the crust of an insect.

This inducer, which can induce the production of the deacetylase, may be added in an amount of from 0.1 to 200 g, preferably from 1.0 to 50 g, per liter of the medium. The content of the inducer may be appropriately selected depending on the physical properties thereof. For example, 16-mesh solid chitin may be added in an amount of 15 g/l, while water-soluble glucosamine may be added in an amount of 50 g/l.

As the carbon source, any substance may be selected so long as the microorganism can metabolize it. For example, at least one substance selected from the group consisting of glucose, maltose, xylose, sucrose and peptone may be employed therefor. Alternately, the aforesaid inducer may also serve as the carbon source.

The carbon source may be added in an amount of from 1 to 200 g, preferably from 4 to 40 g, per liter of the medium.

When the inducer also serves as the carbon source, it may be added in an amount of from 1 to 200 g, preferably from 4 to 75 g, per liter.

As the nitrogen source, at least one substance selected from the group consisting of organic nitrogen sources such as yeast extract, peptone and meat extract and inorganic nitrogen sources such as ammonium sulfate and ammonium chloride may be used. Alternately, the aforesaid inducer may also serve as the nitrogen source.

The nitrogen source may be added in an amount of from 0.5 to 50 g, preferably from 1 to 20 g, per liter of the medium. When the inducer also serves as the nitrogen source, it may be added in the same amount as the one specified above in regard to the use of the inducer also as the carbon source.

As the inorganic salt, at least one substance selected from the group consisting of magnesium sulfate, magnesium chloride, sodium phosphate, potassium phosphate, potassium chloride, sodium chloride and calcium chloride may be used.

The inorganic salt may be added in an amount of from 0.1 to 30 g, preferably from 0.2 to 10 g, per liter of the medium.

In addition to the above-mentioned components, the medium may further contain a gelling agent such as agar or gelatin, if required.

The medium to be used in the present invention may be prepared by adding the above-mentioned components to distilled water, dissolving the soluble components, adjusting the pH value within a range of from 6.5 to 8.0 by using an acid or a base, and then sterilizing by, for example, high-pressure sterilization.

As a particular example of the medium, a liquid medium (pH:7.0) containing 3 g of ammonium nitrate, 1 g of dipotassium hydrogenphosphate, 20 g of sodium chloride, 0.5 g of magnesium sulfate, 0.08 g of calcium chloride and 4 g of chitin, each per liter of the medium, may be cited.

The Vibrio cholerae non-O1 is incubated in the aforesaid medium under aerobic conditions. The incubation temperature ranges from 20° to 38° C., preferably from 3° to 37° C., while the incubation time range from 3 to 140 hours, preferably from 6 to 60 hours. (2) Isolation of deacetylase.

After the completion of the incubation, the culture medium is divided into a solution and cells by any method commonly employed in the art, for example, centrifugation or microfiltration.

Then the target deacetylase can be obtained from the cells thus separated by extracting the cells with a Polymyxin solution or by grinding the cells by a mechanical method and then treating in the conventional manner. For example, the separated cells are added to 10 ml of physiological saline containing 250,000 U of Polymyxin B, shaken at 37° C. for 20 minutes, and centrifuged at 8,000 g for 20 minutes twice. The supernatants thus obtained are combined and dialyzed at 5° C. for 4 hours or longer. Thus the deacetylase can be obtained. (3) Properties of deacetylase The deacetylase produced by the process of the present invention has the following properties. Function:

It deacetylates the acetyl groups of chitin, N-acetylglucosamine or N-acetylglucosamine oligomers so as to give chitosan, glucosamine and glucosamine oligomers. The enzymatic activity of the enzyme obtained from Vibrio cholerae non-O1 for each substrate will be shown in Examples hereinafter.

pH

It is active within the pH range of from 6 to 10.6. A preferable pH range is from 7 to 9.

Temperature

It is active within the temperature range of from 25° to 40° C. A preferable temperature range is from 30° to 37° C.

To further illustrate the present invention in greater detail, the following Examples will be given.

EXAMPLE 1

Vibrio cholerae non-O1-1148A was incubated in a liquid medium (pH: 7.4), which contained 3 g (per liter of the medium, the same will apply hereinafter) of ammonium nitrate, 1 g of dipotassium hydrogenphosphate, 20 g of sodium chloride, 0.5 g of magnesium sulfate, 0.08 g of calcium chloride and 15 g of chitin, at 37° C. under aerobic conditions for 54 hours. Next, the culture medium was centrifuged at 8,000 g for 20 minutes to thereby separate the cells from the culture supernatant.

The cells thus separated were added to 10 ml of physiological saline containing 250,000 U of Polymyxin B and shaken at 37° C. for 20 minutes. After centrifuging at 8,000 g for 20 minutes twice, the obtained supernatants were combined and dialyzed at 5° C. for 24 hours. After centrifuging at 8,000 g for 20 minutes, 9.8 ml of a supernatant was obtained.

To 0.3 ml of this supernatant were added 0.1 ml of a 0.15M phosphate buffer solution (pH: 7.8) and 0.1 ml portions of 7 substrate solutions (concentration: 1%). Thus 7 specimens were obtained. Each specimen was shaken at 32° C. for an hour and the amino sugar thus formed was determined by the indole-HCl method [refer to Z. Dische, E. Borentreund, J. Biol. Chem., 184, 517 (1950)]. Table 1 shows the results which are expressed in enzymatic activities per liter of the culture medium.

TABLE 1

| Substrate | Deacetylase activity (U/l)* |
|---|---|
| N-acetylglucosamine | 13.4 |
| chitobiose (GlcNAc)$_2$ | 10.3 |
| chitotriose (GlcNAc)$_3$ | 9.8 |
| chitotetraose (GlcNAc)$_4$ | 8.8 |
| chitopentaose (GlcNAc)$_5$ | 9.5 |
| chitohexaose (GlcNAc)$_6$ | 7.4 |
| Chitin | 2.2 |

*An enzymatic activity capable of forming 1 microequivalent of amino group within 1 hour is defined as 1 unit (U).

EXAMPLE 2

Vibrio cholerae non-O1-1136B (isolated from seawater) was incubated as a deacetylase-producing bacterium in the same medium as the one employed in the Example 1, except that 15 g of chitin employed as the inducer was replaced with 50 g of N-acetylgucosamine, at 37° C. under aerobic conditions for 24 hours. After performing the same separation procedure as the one described in the Example 1, 10.3 ml of a supernatant containing the target deacetylase was obtained.

To 0.03 ml of this supernatant were added 0.37 ml of 0.05M phosphate buffer solution (pH: 7.8) and 0.1 ml of a 0.1M N-acetylglucosamine solution. After shaking at 32° C. for an hour, the amino sugar thus formed was determined by the indole-HCl method. The enzyme thus obtained showed an activity of 93.0 (U/l).

As described above, the present invention makes it possible to obtain deacetylase by incubating a deacetylase-producing bacterium belonging to Vibrio sp. The deacetylase thus obtained has a substrate specificity and thus can deacetylate chitin, N-acetylglucosamine and oligomers thereof under mild conditions without causing any side reactions. Thus chitosan, glucosamine and oligomers thereof having good qualities can be easily obtained thereby.

As described above, chitosan and glucosamine oligomers have attracted public attention since they have antimicrobial and antitumor activities and are available as an elicitor. Therefore it is expected that the deacetylase obtained by the process of the present invention is widely applicable.

For example, it is reported that the addition of 0.01% of chitosan retards the growth of *Escherichia coli* by 2 days and that the addition of 0.02% thereof completely inhibits the growth of this bacterium. Namely, chitosan is effective in suppressing the growth of bacteria.

It is also reported that chito-oligosaccharide hexamer has a potent immunopotentiating effect and a high antitumor activity.

Furthermore, it is reported that chitosan serves as an elicitor for the production of phytoalexins which are formed by vegetable cells in order to prevent the growth of pathogenic microorganisms.

Chitosan oligosaccharides are advantageous in that the aforesaid effects can be easily utilized since they are highly soluble.

What is claimed is:

1. A process for producing deacetylase, which comprises incubating deacetylase-producing cells of *Vibrio cholerae* IFO-15429 in a culture medium containing a carbon source, a nitrogen source, an inorganic salt and an inducer selected from the group consisting of chitin, chitin-containing materials, N-acetylglucosamine and N-acetylglucosamine oligomers, separating said Vibrio cells from the culture medium and isolating the deacetylase from the cells separated from said culture medium.

* * * * *